United States Patent
Oldani

(10) Patent No.: US 7,835,567 B2
(45) Date of Patent: Nov. 16, 2010

(54) VISUAL FIBER PLACEMENT INSPECTION

(75) Inventor: Tino Oldani, Rockford, IL (US)

(73) Assignee: Ingersoll Machine Tools, Inc., Rockford, IL (US)

( * ) Notice: Subject to any disclaimer, the term of this patent is extended or adjusted under 35 U.S.C. 154(b) by 968 days.

(21) Appl. No.: 11/656,768

(22) Filed: Jan. 23, 2007

(65) Prior Publication Data

US 2007/0173966 A1  Jul. 26, 2007

Related U.S. Application Data

(60) Provisional application No. 60/761,664, filed on Jan. 24, 2006.

(51) Int. Cl.
  *G06K 9/62* (2006.01)
(52) U.S. Cl. .................................... 382/152
(58) Field of Classification Search .................. None
  See application file for complete search history.

(56) References Cited

U.S. PATENT DOCUMENTS

| | | | | |
|---|---|---|---|---|
| 5,266,139 A | * | 11/1993 | Yokota et al. | 156/169 |
| 5,475,766 A | * | 12/1995 | Tsuchiya et al. | 382/144 |
| 5,562,788 A | * | 10/1996 | Kitson et al. | 156/64 |
| 6,072,897 A | * | 6/2000 | Greenberg et al. | 382/144 |
| 6,799,081 B1 | * | 9/2004 | Hale et al. | 700/98 |
| 6,814,822 B2 | | 11/2004 | Holmes et al. | |
| 2002/0141632 A1 | * | 10/2002 | Engelbart et al. | 382/141 |
| 2005/0236735 A1 | | 10/2005 | Oldani et al. | |
| 2005/0240291 A1 | | 10/2005 | Oldani et al. | |
| 2005/0247396 A1 | | 11/2005 | Oldani et al. | |
| 2005/0269016 A1 | | 12/2005 | Oldani et al. | |
| 2006/0070697 A1 | | 4/2006 | Hoffmann | |
| 2007/0204555 A1 | | 9/2007 | Engelbart et al. | |
| 2007/0229805 A1 | | 10/2007 | Engelbart et al. | |

FOREIGN PATENT DOCUMENTS

CA    2 435 532 A1    2/2004

OTHER PUBLICATIONS

Russell Devlieg et al., High-Speed Fiber Placement on Large Complex Structures, paper, 2007, 5 pages, 2007-01-3843.

* cited by examiner

*Primary Examiner*—Brian P Werner
(74) *Attorney, Agent, or Firm*—Reinhart Boerner Van Deuren P.C.

(57) ABSTRACT

An apparatus and method are provided for performing, on-the-fly, real time inspection of a composite structure formed by an automated fiber placement machine, through comparison of a visual image of at least a portion of the composite structure to a virtual image of the composite structure. Proper formation of the structure, and/or anomalies within the structure, are determined by comparing the visual image to the virtual image. The automated fiber placement machine, and/or tooling upon which the fiber is placed, are manipulated, and a visual indicator are provided to facilitate inspection and/or repair of any detected anomalies during fabrication of the composite structure.

6 Claims, 3 Drawing Sheets

FIG. 3
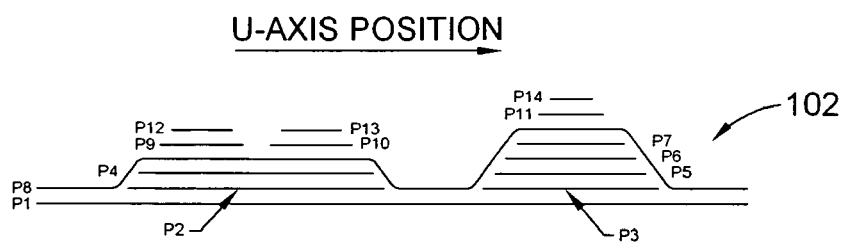
FIG. 2
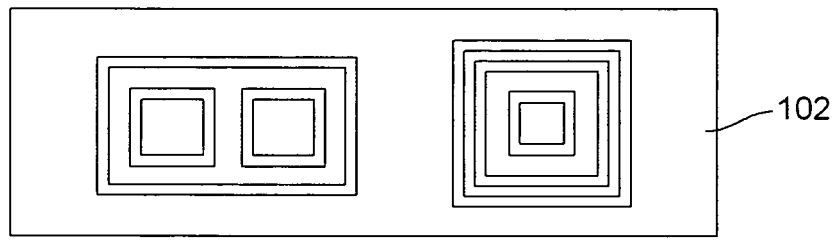
| SEQUENCE | PLY | ORIENT | MATERIAL |
|---|---|---|---|
| S1 | P1 | 0 | M1 |
| S2 | P2 | 45 | M1 |
|    | P3 | 45 |    |
| S3 | P4 | 90 | M1 |
|    | P5 | 90 |    |
| S4 | P6 | -45 | M1 |
| S5 | P7 | 0 | M1 |
| S6 | P8 | 90 | M1 |
| S7 | P9 | 45 | M1 |
|    | P10 | 45 |   |
|    | P11 | -45 |  |
| S8 | P12 | -45 | M1 |
|    | P13 | -45 |   |
|    | P14 | 90 |   |
FIG. 4

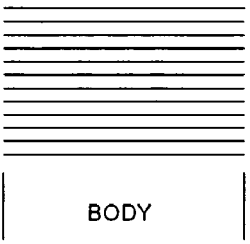
U-AXIS POSITION
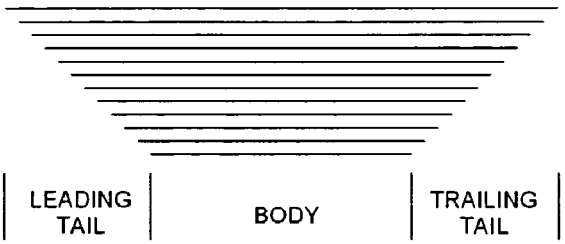
LAYING DIRECTION
FIG. 5A — BODY
FIG. 5G — LEADING TAIL | BODY | TRAILING TAIL
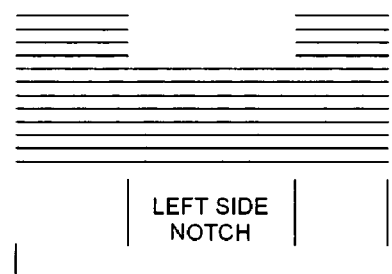
FIG. 5B — LEFT SIDE NOTCH | BREAK | BODY
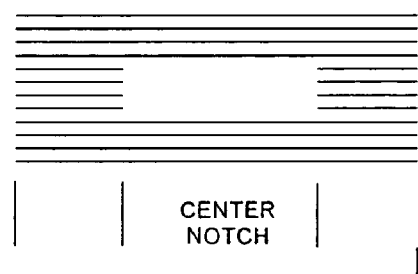
FIG. 5F — CENTER NOTCH
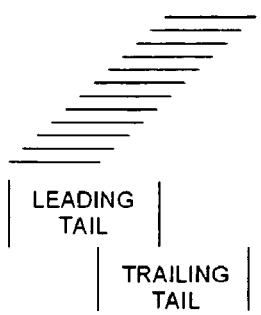
FIG. 5C — LEADING TAIL | TRAILING TAIL
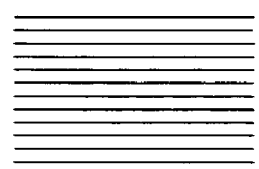
FIG. 5D — FULL-WIDTH COURSE
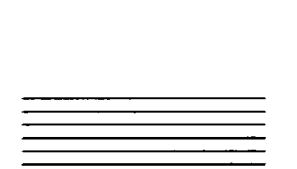
FIG. 5E — LESS-THAN-FULL-WIDTH COURSE | ROLLER WIDTH

VISUAL FIBER PLACEMENT INSPECTION

FIELD OF THE INVENTION

This patent application claims the benefit of U.S. Provisional Patent Application No. 60/761,664, filed Jan. 24, 2006, the disclosure and teachings of which are incorporated herein in their entireties.

This invention is related to the use of automated fiber placement machines for fabrication of composite structures, and more particularly to performing visual inspection of the composite structure during the automated fiber placement process.

BACKGROUND OF THE INVENTION

Automated fiber placement is a process that is widely used for fabricating composite structures from pre-impregnated composite materials, such as carbon fiber, fiber glass and Kevlar. The materials, for use in automated fiber placement, typically take the form of a strip or yarn of composite material impregnated with a resin, with such strips or yarns being commonly referred to as tapes or tows, those terms being used in a generally interchangeable manner herein.

During automated fiber placement, groups of tows or tapes are deposited on a mold or tool by an automated fiber placement machine, to form a composite structure. The fiber placement machine typically includes a computer controlled, robotic, fiber placement head which has provisions for simultaneously handling groups of, for example, 12, 24, or 32 tows, which are positioned substantially parallel to one another by the fiber placement head to form a substantially contiguous band, of pre-impregnated composite material. Often, one or more bands of material form a layer or ply of material, having the tows in the ply oriented substantially parallel to one another in the ply. Successive plys may be laid on top of a preceding ply, with the tows in the successive plys being oriented in a different direction than adjacent plys, to create a completed part having desired structural capabilities.

During the fiber placement process, it is sometimes necessary to cut and stop the feed of individual tows, thus removing them from the band of material, in order to reduce the width of the band so that it may be placed onto the surface of the mold or tool in a manner that precludes having excessive gaps between successive bands of material, or having the edges of successive bands of material unintentionally overlap one another. In similar fashion, it is often desirable to add tows to the band in order to increase its width, at various stages of the automated fiber placement process, in order to facilitate manufacture of the composite structure. The process of removing or adding tows is commonly referred to "cut and add". On large structures, it may also be necessary to periodically splice in fresh tows during fabrication, from replacement reels of material, as the material on the original supply reel is exhausted.

Automated fiber placement machines are capable of depositing material onto a tool surface at high feed-rates, of, for example, 1200 inches/minute or higher. For maximizing productivity, it is desirable to operate an automated fiber placement machine at such high feed-rates throughout the fabrication of a composite structure. It is highly desirable, therefore, that automated fiber placement machines be capable of modifying the width of the band of material being applied without stopping, or slowing down, the machine to cut or add tows to the material band. In the vernacular of the automated fiber placement industry, it is highly desirable that automated fiber placement machines be capable of cutting or adding tows "on-the-fly."

From the foregoing description, it will be appreciated that fabrication of a composite structure by automated fiber placement is a highly complex process, requiring considerable upfront effort during design of the structure, associated production tooling, and in setting up the automated fiber placement machine, to ensure that each and every tow of material is properly placed during the automated fiber placement process, in a manner that will result in a structure having a desired geometry and structural properties. Due to the complexity involved in both the design and production of the composite structure by automated fiber placement, it is common practice to utilize computerized tools for both designing the structure, and in programming the automated fiber placement machine to properly move and operate the robotic fiber placement head, feed out material, cut and add tows, and in some cases to also move the tooling in synchronization with the robotic head during automated lay-up of the composite structure on the tooling. The process of designing a composite structure for automated fabrication is discussed in U.S. Pat. No. 6,799,081 B1, to Hale et al.

Even after the composite structure, the tooling, and the automated fiber placement machine are designed and set up to provide for proper placement of the tows during fabrication, problems inherent in the production of composite structures make it necessary that the resulting composite structure be closely inspected to ensure that each and every tow was indeed properly placed during fabrication. It is necessary, for example, to ensure that tows and/or bands of tows were properly cut and/or added at a desired location during fabrication of the structure. It is also necessary to detect any improper placement, and/or other anomalous conditions, such as fiber twists, excessive resin build-up, "fuzz balls," bad sections of tow, foreign matter and/or unintended gaps or overlapping of the tows.

Although it is highly desirable to perform such inspection on-the-fly in real-time, during automated fiber placement, factors such as the high speed at which the automated fiber placement takes place, complex shaped and large sized composite structures, and rapid movement of the robotic fiber placement head makes such real-time inspection very difficult. In the past, the difficulty involved has, substantially, precluded real-time, on-the-fly, inspection, and required reliance on methods which could only be carried out after the structure is completely fabricated, or requiring that the automated fiber placement process be stopped for a period of time to allow inspection by visual, sonic, magnetic resonance imaging, or x-ray to determine the location of the anomalies.

It is also desirable that the inspection be carried out in real-time, and that the results of the inspection be available substantially in real-time, while the composite structure is being fabricated, so that any anomalies or other problems discovered during inspection may be repaired, or otherwise dealt with, prior to completion of fabrication of the composite structure.

In one prior attempt at performing such real-time inspection, disclosed in U.S. Pat. No. 5,562,788 to Kitson et al., a visual imaging system utilizes a laser analog displacement sensor to detect the edges of individual composite tows, and utilizes the location of the edges of the individual tows, to compute the location and size of gaps between the individual tows. The location and size of the computed gaps between the tows is then utilized as an indicator for flaws, such as excessive gaps, overlaps, twisted tows, or the presence of foreign material under the tow. Because Kitson '788 relies solely upon computations based on the sensed edges of the individual tows, only an approximation of any anomalous condition is provided. Conditions such as fiber twists, excessive resin buildup, or fuzz balls, for example, are not directly detected by the methods and apparatus of Kitson. The methods and apparatus of Kitson also require that massive amounts of data be collected, stored, and analyzed.

All of the challenges and problems discussed above are exacerbated in structures, such as aircraft flight surfaces and entire fuselage sections, of the type being utilized in modern military and commercial aircraft. Due to their large size and complexity, and the necessity for providing substantially infallible structural integrity under high loading conditions, it is highly desirable that inspection processes be carried out in real-time, during fabrication of the composite structure by automated fiber placement, so that any anomalous conditions can be identified and potentially rectified prior to continuing with the fabrication process. Due to the complex nature of the three dimensional placement of the tows, and multi-axis motions of the tooling and robotic fiber placement head during fabrication, it is also highly desirable that a method and apparatus be provided for indicating the location of any detected anomalies, and/or properly positioning the composite structure to allow any additional inspection or corrective action to be conveniently made once an anomalous condition is detected. Prior inspection systems, such as the one disclosed by Kitson '788 do not provide for such convenient additional in-process inspection and corrective action.

In order to address the unique problems of fabricating very large composite structures, such as aircraft control surfaces and fuselages, for example, the Assignee of the present invention has developed a number of advanced capabilities, including the use of multiple robotically controlled fiber placement heads, and automatically replaceable creels for holding spools of the pre-impregnated composite material. These and other advanced methods and apparatuses for performing automated fiber placement are disclosed in a number of the Assignee's related published U.S. patent applications, such as: 2006/0070697 A1, to Hoffmann, titled, METHOD AND APPARATUS FOR DIRECTING RESIN-IMPREGNATED TAPE; 2005/0247396 A1, to Oldani et al., titled, AUTOMATED FIBER PLACEMENT USING MULTIPLE PLACEMENT HEADS, REPLACEABLE CREELS, AND REPLACEABLE PLACEMENT HEADS; 2005/0236735 A1, to Oldani et al., titled, FORMING A COMPOSITE STRUCTURE BY FILAMENT PLACEMENT ON A TOOL SURFACE OF A TABLET; 2005/0269016 A1, to Oldani et al., titled, AUTOMATED FORMING OF A PRE-IMPREGNATED COMPOSITE STRUCTURAL ELEMENTS; and 2005/0240291 A1, to Oldani et al., titled PERFORMING HIGH-SPEED EVENTS "ON-THE-FLY" DURING FABRICATION OF A COMPOSITE STRUCTURE BY AUTOMATED FIBER PLACEMENT.

Prior inspection methods and apparatuses, including Kitson '788, do not address the additional complexity and unique problems involved in performing inspection where advanced, state-of-the-art, methods and apparatuses, of the type described in the Assignee's patent applications listed above are utilized.

What is needed, therefore, is an improved method and apparatus for performing high-speed inspection, preferably on-the-fly, in real time, during fabrication of a composite structure by automated fiber placement. It is also desirable that such an improved apparatus and method include provisions for indicating the location of any anomalies during fabrication, to allow for additional inspection and possible in-process correction. It is further desirable that such improved methods and apparatuses provide for post processing to record one or more of: proper and/or improper placement of the fibers; and/or anomalies detected. It is yet further desirable that an improved apparatus and/or method provide images displaying some or all anomalous conditions detected.

BRIEF SUMMARY OF THE INVENTION

The invention provides an improved method and apparatus for inspecting a composite structure formed by an automated fiber placement machine, by comparing a visual image of at least a portion of the structure to a virtual image of the structure. Proper formation of the structure may be verified by comparing the visual image to the virtual image. Alternatively, improper formation of a portion of the structure may be determined by comparing the visual image to the virtual image.

The invention may further include manipulating the automated fiber placement machine, and/or tooling upon which the fiber is placed, to facilitate inspection and/or repair of an improper formation.

The invention may also provide a visual indication of a detected imperfection. In some forms of the invention, the visual indication includes providing a location of the imperfection on the structure. A visible indication of the location of the imperfection may be provided by an appropriate method, such as illuminating the imperfection with a light source, such as a laser pointer. In some forms of the invention, the structure and/or at least a portion of the automated fiber placement machine and/or tooling may be moved to a position whereat the imperfection may be indicated by a laser pointer, or other light source, directed by the automated fiber placement machine.

Where the invention is practiced to form a composite structure having one or more courses and/or plies including multiple tows, the invention may further include comparing the visual image of the tows in a given course and/or ply to a virtual image of the tows in the given course or ply.

In some forms of the invention, the visual image provides a two dimensional profile plot of an outer surface of the tows in the given ply.

In some forms of the invention, an automated fiber placement machine includes a fiber placement head, and the visual image is sensed by a vision capture element operatively attached to, the fiber placement head. In some forms of the invention, the vision capture element may be mounted directly on the fiber placement head.

Where the fiber placement head includes a feed device for feeding out one or more tows of material, the invention may further include operatively connecting a motion sensor to the feed device for synchronization of the visual image with the virtual image.

In one form of the invention, a composite programming system (CPS) determines where all tows will be dropped and/or added to meet boundary and interband gap/overlap criteria set out by the designer of a composite structure. Outputs of the CPS include: 1) an NC (numerical control) file representing the path of a compaction roller in a fiber placement head of a fiber placement machine; and 2) a virtual image, in the form of a theoretical ply profile representing each band of tows as it is laid, as a course, onto the surface of a tool, or the surface of a previously laid ply of the composite structure. The NC file is sent to a Machine Control System (MCS), and the theoretical ply profile is sent to a composite comparison device (CCD). The MCS processes the commands in the NC file to drive the fiber placement machine and/or a tool in such a manner as to lay a tow, or band of tows, at a desired location on the tool. The MCS also provides synchronization commands to the CCD, so that both the MCS and the CCD can be calibrated to the same position along each course. While the ply is being laid, the CCD captures an image of the actual lay-up surface. The CCD may then compare the actual ply profile, from the image, to the theoretical ply profile, to detect and record any discrepancies between the actual and theoretical ply profiles, and may also produce a file for a variety of future uses, such as transferring the results to the MCS, which may then be utilized to guide an operator of the fiber placement machine to each anomaly location, for repair or any other action that may be deemed appropriate.

Some forms of the invention include multiple fiber placement heads, with each fiber placement head having operatively attached thereto a separate vision capture element. The visual images provided by the separate vision capture elements may be provided to a single, common, CCD. Alternatively, each vision capture element may be attached to a separate CCD, dedicated to that particular vision capture element.

Some forms of the invention may also include replaceable creels and/or replaceable fiber placement heads. Some forms of the invention may include the capability to generate images of any anomalous condition identified through practice of the invention.

In some forms of the invention, the virtual image defines a so called "U" axis position, associated with movement of a feed roller of the fiber placement head, during fabrication of the composite structure by the automated fiber placement machine. In some forms of the invention, the "U" axis position may be reset for each course. The location of an anomaly, or of any particular point within the composite structure, may be identified by a linear dimension along the "U" axis in a given course, in combination with a ply number of the virtual image. Incorporation of the "U" axis into the invention, thus provides an efficient and effective mechanism for locating a particular point in the composite structure, in a manner which greatly facilitates identification of the location of an anomaly, for example, or movement of the automated fiber placement machine and/or the tool upon which the composite structure is being formed, to facilitate off-line inspection and/or repair of the anomaly.

An apparatus for inspecting a composite structure formed from one or more composite tows by an automated fiber placement machine, may include, a composite comparison device (CCD), for comparing a visual image of at least a portion of the composite structure to a virtual image of the at least a portion of the composite structure. The apparatus may also include a vision capture element, for taking a visual image of a ply profile in the at least a portion of the composite structure, in real-time, on-the-fly, as the ply is laid down by the automated fiber placement machine, and for providing the visual image to the CCD.

The invention may be practiced with a variety of different types of vision capture sensors, including: laser sensors; cameras; two dimensional and three dimensional sensors; scanners; etc. The term "vision capture element" as used herein, is intended to encompass any appropriate sensing and/or detection devices that may be used for generating the visual image to be used in practicing the invention.

Regardless of the particular type of sensing or detection device used in practicing the invention, a visual image, as viewed by the sensing or detection device, is processed in an entirely different, elegantly simple, and straightforward way, in the present invention as compared to prior art, such as Kitson, to substantially directly compare an overall viewed image of an area of the composite structure to a virtual overall image of the same area, in a manner that eliminates the need for tedious computations requiring massive amounts of computer memory required by Kitson. Because the present invention can compare the entire viewed image to the virtual image, the present invention can provide substantially more and better information regarding proper and improper construction of the composite structure than prior methods, such as the method of Kitson which found only the edges of the tows in the viewed area, after arduous computations, with only the computed edge location info then being used as a limited indicator of part quality.

In some forms of the invention, other devices, such as tow-feed sensors may also be utilized for generating information to be used in generating the visual image, comparing the visual and virtual images, or for other purposes in practicing the invention.

An apparatus, according to the invention, may further include, a composite programming system (CPS), and a machine control system (MCS), with the CPS being configured for determining where individual tows, or groupings of tows, will be dropped and/or added to meet boundary and interband gap/overlap criteria set out by a designer of a composite structure, and providing CPS outputs including, a numerical control (NC) file and a theoretical ply profile, the NC file representing the path of a compaction roller in a fiber placement head of a fiber placement machine, and being provided as an input to the MCS, and the theoretical ply profile representing each band of tows as it is laid, as a course, onto the surface of a tool, or the surface of a previously laid ply of the composite structure, and being provided as an input to the CCD. The CPS outputs may also designate where individual tows are to be added, dropped, and/or spliced, to achieve the desired configuration and structural properties in the composite structure.

An MCS, according to the invention, may be configured for utilizing the NC file for driving the fiber placement machine and/or a tool in such a manner as to lay a tow, or band of tows, at a desired location on the tool. The MCS may also be configured for providing synchronization commands to the CCD, so that both the MCS and the CCD can be calibrated to the same position along each course.

A CCD, according to the invention, may be configured for capturing a visual image of the actual lay-up surface of the tows, as they are laid down by the placement head, and for comparing the actual ply profile as captured in the visual image to the theoretical ply profile.

A method, according to the invention, for inspecting a composite structure, formed by an automated fiber placement machine from a plurality of fiber tows laid down by the automated fiber placement machine, may include: constructing a virtual image of the structure, prior to forming the composite structure, defining a proper placement and configuration of each of the plurality of fiber tows within the composite structure; taking a visual image of the appearance of the tows forming at least a portion of the composite structure, in real time, as the composite structure is formed by the automated fiber placement machine; and then comparing the visual image of the appearance of the tows in the at least a portion of the structure to the proper configuration and placement of the fiber tows as defined in the virtual image of the at least a portion of the composite structure.

The invention may also take the form of a computer-readable medium having computer executable instructions for performing one or more steps of a method, according to the invention.

Other aspects, objectives and advantages of the invention will be apparent from the following detailed description and accompanying drawings.

BRIEF DESCRIPTION OF THE DRAWINGS

The accompanying drawings, forming a part of the specification, illustrate several aspects of the present invention and, which, together with the description, serve to explain the invention. In the drawings:

FIGS. 2-4 are, respectively, a top plan view, a side elevation view, and a ply chart for an exemplary composite structure of the type which might be inspected using an apparatus and/or method according to the invention.

FIGS. 5A-5G are schematic illustrations of exemplary courses of fiber tows, of the type which might be inspected utilizing an apparatus and/or method according to the invention.

Figure 1:
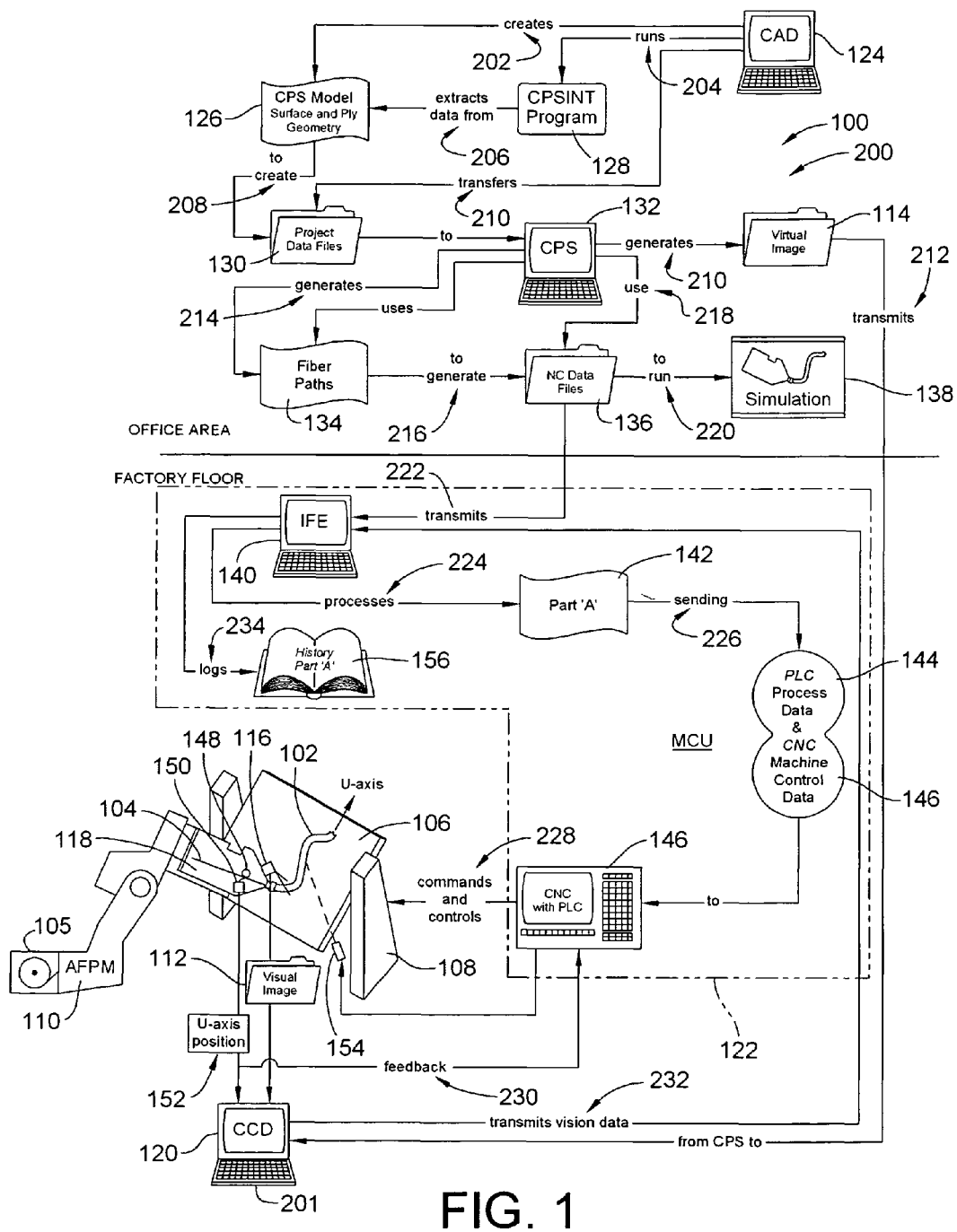
FIG. 1 is a combined schematic and flowchart illustration of an exemplary embodiment of a method and apparatus, according to the invention, which provides on-the-fly, real time inspection of a composite structure formed by an automated fiber placement machine, by comparing a visual image of at least a portion of the structure to a virtual image of the at least a portion of the structure.

While the invention will be described in connection with certain preferred embodiments, there is no intent to limit it to those embodiments. On the contrary, the intent is to cover all alternatives, modifications and equivalents as included within the spirit and scope of the invention.

DETAILED DESCRIPTION OF THE INVENTION

FIG. 1 is a combined schematic and flowchart illustrating a first exemplary embodiment of an apparatus 100 and a method (200) for inspecting a composite structure 102, formed from one or more composite tows 104, fed from a creel 105, and laid onto a tool surface 106 of a moveable tool 108 by an automated fiber placement machine (AFPM) 110, by comparing (201) a visual image 112 of at least a portion of the composite structure 102 to a virtual image 114 of the portion of the composite structure 102 captured in the visual image 112.

As will be described in more detail below, the virtual image 114 provides a theoretical rendering of the way that each tow in each layer of the composite structure should appear, in accordance with the design of the structure 102, to a vision capture element 116, which is operatively or physically mounted to a fiber placement head 118 of the AFPM 110, to view the fiber tows 104, as they are sequentially laid onto the tool surface 106 or on top of previously laid courses of the fiber tows 104 of the composite structure 102. The visual and virtual images 112, 114 are fed to a composite comparison device (CCD) 120, for comparison of the visual image 112 to the virtual image 114. The composite comparison device (CCD) 120 compares the visual and virtual images 112, 114, and provides a variety of outputs, in various embodiments of the invention, indicating proper, and/or improper formation of the composite structure 102, as compared to a theoretical "perfectly constructed" composite part, as construed by the designers of the composite part, and utilized for generating the virtual image 114, according to the invention.

As shown in FIGS. 2-4, a typical composite structure, of a type which might benefit from inspection using an apparatus or method according to the invention, consists of a plurality of layers, or courses, consisting of multiple bands of fiber tows, which are sequentially laid down onto the tool surface 106 in a variety of patterns to form the composite structure 102. Specifically, FIGS. 2 and 3 are top and side-elevation views, respectively, of a representative composite part 102, constructed of multiple sequences of multiple plies, in accordance with a ply table shown in FIG. 4.

As will be understood, from an examination of FIGS. 2-4, the plies P1-P14, are sequentially laid down in a series of passes by the fiber placement head 118 across the tool surface 106, with the sequences being indicated by reference numerals S1-S8, to indicate that the first sequence S1 including only one ply, P1, is laid down, followed by the second sequence S2, which includes plies P2 and P3, etc., through sequence S8, consisting of plies P12, P13, and P14. As further shown in the ply table of FIG. 4, each of the plies P1-P14 may have a varying orientation, with the exemplary ply table of FIG. 4 showing orientations of 0, +/−45 and +/−90 degrees. In the exemplary embodiment of FIG. 4, as shown in the material column of FIG. 4, all of the plies P1-P14 of the exemplary embodiment shown in FIGS. 2 and 3 are constructed of the same material M1. It will be understood, however, that in other embodiments of the invention the material utilized for each of the plies P1-P14 may be different.

As shown in FIGS. 5A-5G, a given course of plies laid down in each sequential pass of the fiber placement head 118 over the tool surface 106 may constitute a full-width course, a less-than-full-width course, and may be otherwise configured with leading or trailing tails, left and/or right side notches, breaks, and/or center notches.

The visual and virtual images 112, 114 of the invention, are calibrated to one another, in the exemplary embodiment of the invention, by reference to the same course number, ply number, and a so-called "U-axis position," used by a machine control unit (MCU) 122 during formation of the composite structure 102, for controlling the motion of the automated fiber placement machine (AFPM) 110 and the moveable tool 108 and feeding of the composite tows 104 onto the tool 106, or a previously laid down tow 104.

By virtue of this arrangement, the invention allows a substantially literal comparison to be made by the CCD 120 between the virtual image 114, for a portion of the virtual image 114 within view of the vision capture element 116, and the actual visual appearance of the portion of the composite structure 102 within view of the vision capture element at a particular location within the composite structure 102.

As shown in FIG. 1, the various steps of the inspection method 200, according to the invention, may be carried out partially in an office area and partially on the factory floor for convenience, depending upon the particular circumstances surrounding practice of the invention.

Computer aided design (CAD) hardware, software and/or methods 124 are used to create (200) a composite programming system model (CPSM), which includes definition of supporting geometries and CPST. The supporting geometries may include definition of: the tool surface; intermediate surfaces; core insert surfaces; boundaries; points; vectors; curves; and axes. The CPS tables define lay-up order and reference elements within the design model.

The CAD device, methods, and/or software 124 also runs (204) a composite programming system interface program (CPSINT 128), with the CPSINT program 128 extracting data (206) from the CPS model 126 to create (208) project data files 130. The CAD device, method, and/or software 124 also transfers (210) the project data files 130 to a composite programming system (CPS) device and/or software 132, which generates 210 the virtual image 114 from the project data files, and transmits (212) the virtual image to the CCD 120.

The CPS 132 also generates (214) fiber paths 134, and generates (216) numerical control data files (NC Data Files 136). The CPS 132 may also use 218 the NC Data Files 136 to run (220) a simulation, to verify or modify the fiber paths or other information in the NC Data Files 136.

The CPS 132 then transmits (222) the NC Data Files 136 to an intelligent front end (IFE) device and/or software, which forms part of the machine control unit (MCU 122), of the exemplary embodiment of the inspection apparatus 100, according to the invention. The IFE 140 processes (224) the NC Data Files 136, received from the CPS 132, and sends a processed file for the composite structure 102 (referenced as part 'A' in FIG. 1) including programmable logic control (PLC) process data 144 and computer numerical control (CNC) machine control data 146 to a computer numerical control (CNC) device and/or software 146, which is part of the machine control unit 122 of the exemplary embodiment of the inspection apparatus 100, according to the invention.

The CNC 146 utilizes the PLC process data 144 and CNC machine control data 146 for commanding and controlling the automated fiber placement machine 110 and the moveable tool 108. In addition to controlling the relative positions of the AFPM 110 and the tool surface 106 of the moveable tool 108, in such a manner that a compaction roller (not shown) in the automated fiber placement head 118 is moved across the tool surface in an appropriate manner during formation of the composite structure, the CNC 146 also controls the motion of a plurality of feed rollers 148, within the fiber placement head 118, in such a manner that the individual fiber tows are fed by the feed rollers to the compression roller at appropriate times during construction of the composite structure 102 along the U-axis, with the U-axis being defined substantially as a line formed in a direction substantially perpendicular to a rotational axis of the feed rollers 148, as the fiber placement head 118 is moved with respect to the tool surface 106 by the AFPM 110, during construction of the composite structure 102.

As is known in the art, the CNC 146 commands the feed rollers 148, in conjunction with other elements within the fiber placement head 118, to add and/or cut the various individual tows 104 at selective positions along the U-axis, during each sequence of motion of the fiber placement head across the tool surface 106 in which the fiber placement head is laying down one or more courses or tows, to properly place the tows and/or courses in desired patterns and orientations, such as those described above in relation to FIGS. 2-4, and FIGS. 5A-5E.

To provide synchronization between the virtual image 114, generated by the CPS 132, and the visual image 112 recorded by the vision capture element 116, the exemplary embodiment of the inspection apparatus 100 includes an encoder 150, operatively attached to the feed rollers 148, for detecting and transmitting to the CCD 120 the U-axis position corresponding to the portion of the composite structure 102 within view of the vision capture element 116. The CCD 120 uses the U-axis position 152 from the encoder 150 to synchronize the visual image 112 with the same U-axis position of the virtual image 114, for a given course of the composite structure 102, to thereby make a substantially instantaneous real-time, on-the-fly comparison between the visual and virtual images 112, 114. In the exemplary embodiment of the inspection apparatus 100 and method 200, it is contemplated that the U-axis position would be reset to a starting position for each successive sequence of laying down a course of fiber tows during construction of the composite structure.

The U-axis position 152 is also fed back 228 to the CNC 146, for use by the CNC in commanding and controlling the AFPM 110, the moveable tool 108, and/or a laser pointing device 154, of the exemplary embodiment of the inspection apparatus 100, which may be operated by the CNC 146 to point to areas of the composite structure 102, to thereby facilitate an operator in locating a particular point within the composite structure.

It is contemplated, for example, that the laser pointer might be utilized to pinpoint the location of a discrepancy between the visual and virtual images 112, 114, to thereby help the operator to quickly inspect the indicated area and determine whether corrective action might need to be taken before proceeding with forming the composite structure 102. It is further contemplated, that the laser pointer 154 might also be useful in facilitating and expediting other operations during the formation of the composite structure, such as pinpointing locations at which localized reinforcements, cores, etc. might need to be manually inserted by the operator.

It will be understood, by those having skill in the art, that devices other than laser pointers might also be used for providing a visible indication of a particular location on the composite structure 102. It is also contemplated, that in some embodiments of the invention, multiple laser pointers, or other visual indicating devices, may be utilized either individually or in combination to point to a particular position on the composite structure which might be located out of a direct line of sight with a given one of the indicating devices. It is further contemplated, that in some embodiments of the invention, the CNC 146 may send coordinated command and control signals to the AFPM 110, the moveable table 108 and the laser pointer 154, to move the composite structure 102 to a position whereby the laser pointer 154 can illuminate the particular area of interest on the composite structure 102. In some embodiments of the invention, a laser pointer, or other illumination device might be mounted on a fiber placement head, a separate stand, or even be wireless and hand-held in practicing the invention.

As further shown in FIG. 1, the CCD 120 transmits the visual image data back to the IFE 140, so that the IFE 140 can log 234 the visual image data 112 in a history 156 of the composite structure 102, or generate an image on a computer screen, for example, of any anomaly or area of interest recorded in visual image data 112.

It is contemplated that the history 156 may include a variety of useful information, in various embodiments of the invention. For example, where the CCD 120 determines that the visual image 112 corresponds exactly, or within prescribed tolerances of, the virtual image 114, the visual image might simply be stored with the history 156 as part of the overall documentation relating to successful construction of the composite structure 102. Such records are commonly produced, and archived, within the aerospace industry, in particular those having skill in the art will recognize that the invention provides an efficient and effective method and apparatus for compiling and saving such information. Where the CCD 120 encounters discrepancies between the visual and virtual images, the history 156 may also include further records with regard to the extent of the discrepancy, and records of any corrective action or other activities performed by the operator following notification by the CCD 120 of the presence of the discrepancy.

It will also be noted, by those having skill in the art, that an apparatus and/or method, according to the invention, may be utilized in automated fiber placement operations having multiple automated fiber placement machines or fiber placement heads simultaneously, or sequentially applying courses of fiber during construction of the composite structure. In such embodiments, or in embodiments having replaceable creels, outputs of multiple vision capture elements 116 may be fed to a common CCD 120, or alternatively, multiple CCDs 120 may be utilized for processing the visual image 112 from each vision capture element 116.

By virtue of the comparison, the proper placement of the tows may be verified. The comparison between the virtual and actual images of the outer surfaces of the tows can also be set up to detect and record only discrepancies between the actual and theoretical ply profiles, rather than verifying proper placement of all tows. Although it is contemplated that it will generally be preferable to verify proper placement of all tows, in certain circumstances, such as where computer storage or processing capability are limited, it may be desirable to focus only on any discrepancies detected.

Data collected during the comparison process may also be stored in a form suitable for a variety of uses, such as transferring the results to the MCS, with the MCS then utilizing the stored data to guide the operator of the fiber placement machine to the location of any anomaly detected by the comparison, to facilitate repair of the anomaly or any other action that may be deemed appropriate.

In the exemplary embodiment of the invention, shown in FIG. 1, a vision capture element is mounted directly on a fiber placement head of the fiber placement machine, in close proximity to a compaction roller of the fiber placement head, to thereby provide a visual image of the outer surfaces of the composite tows at a position, as close as reasonably possible, to the point at which the tows are pressed onto the surface of the tool by the compaction roller. The vision capture element of the exemplary embodiment, utilizes a spread beam, which provides a two dimensional linear profile image of a portion of the composite structure, which may extend across a number of tows and/or bands of the composite materials in a given course of material, as it is being laid onto the tool. In other embodiments of the invention, however, any other type of appropriate vision capture element may be used. Vision capture elements having three dimensional, or greater, capability may also be used in some embodiments of the invention.

In some embodiments of the invention, certain types of anomalies, such as defective tows, may also be detected, using appropriate sensing methods, before the tow is placed on the toll surface by the compaction roller.

In the exemplary embodiments of the invention shown in FIG. 1, the fiber placement head, of the automated fiber placement machine, includes one or more feed rollers, for feeding tows of composite material to the compaction head, when directed to do so, in accordance with the process and machine control data supplied to a Computerized Numerical Control (CNC), with the CNC, in turn, providing commands and controls to the automated fiber placement machine. A rotational sensor, in the form of an encoder, is operatively attached to the feed roller, to detect and provide a U-axis position of each tow within each course of the composite structure. Through use of the U-axis position data, in combination with a ply number and course number from the virtual image, the precise location of any particular point within the composite structure may be identified by a linear dimension along the U-axis.

Those having skill in the art will readily recognize that in various embodiments of the invention, specific elements of the invention shown in FIG. 1, or within the scope of the invention as described herein, may be combined with one another and/or connected in arrangements differing somewhat, or even significantly, from the exemplary embodiment shown in FIG. 1 and described above.

All references, including publications, patent applications, and patents cited herein are hereby incorporated by reference to the same extent as if each reference were individually and specifically indicated to be incorporated by reference and were set forth in its entirety herein.

The disclosure and teachings of the following published U.S. patent applications, of the Assignee, are expressly incorporated herein, in their entireties, by reference: 2006/0070697 A1, to Hoffmann, titled, METHOD AND APPARATUS FOR DIRECTING RESIN-IMPREGNATED TAPE; 2005/0247396 A1, to Oldani et al., titled, AUTOMATED FIBER PLACEMENT USING MULTIPLE PLACEMENT HEADS, REPLACEABLE CREELS, AND REPLACEABLE PLACEMENT HEADS; 2005/0236735 A1, to Oldani et al., titled, FORMING A COMPOSITE STRUCTURE BY FILAMENT PLACEMENT ON A TOOL SURFACE OF A TABLET; 2005/0269016 A1, to Oldani et al., titled, AUTOMATED FORMING OF A PRE-IMPREGNATED COMPOSITE STRUCTURAL ELEMENTS; and 2005/0240291 A1, to Oldani et al., titled PERFORMING HIGH-SPEED EVENTS "ON-THE-FLY" DURING FABRICATION OF A COMPOSITE STRUCTURE BY AUTOMATED FIBER PLACEMENT.

Those having skill in the art will recognize that the invention may find particular efficacy in complex applications, such as those disclosed in the above listing of the Assignee's published patent applications, using multiple AFPMs, multiple fiber placement heads, and/or replaceable creels, and/or replaceable heads, due to the extra complexity of tool paths, the necessity for making coordinated cuts and splices, etc., during fabrication of the composite structure.

From the foregoing, those having skill in the art will recognize that the invention provides an efficient and effective method and apparatus for performing high-speed inspection, on-the-fly, in real time, during fabrication of a composite structure by automated fiber placement. Those having skill in the art will also recognize that, by using a comparison of an actual visual image of an area of the composite structure to a virtual image of a theoretically perfect virtual image of the same area, the invention provides a substantially more efficient and effective method and apparatus for inspecting a composite structure, during fabrication of the structure, that prior art methods and apparatuses, such as those disclosed in the Kitson '788 reference discussed above.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An apparatus for inspecting a composite structure formed from one or more composite tows by an automated fiber placement machine, the apparatus comprising:
    a composite comparison device (CCD), for comparing a visual image of at least a portion of the composite structure to a virtual image of the at least a portion of the composite structure;
    a composite programming system (CPS); and
    a machine control system (MCS);
    the CPS being configured for determining where all tows will be dropped and/or added to meet boundary and interband gap/overlap criteria set out by a designer of a composite structure, and providing CPS outputs including, a numerical control (NC) file and a theoretical ply profile;
    the NC file representing the path of a compaction roller in a fiber placement head of a fiber placement machine, and being provided as an input to the MCS;
    the theoretical ply profile representing each band of tows as it is laid, as a course, onto the surface of a tool, or the surface of a previously laid ply of the composite structure, and being provided as an input to the CCD;
    the MCS being configured for utilizing the NC file for driving the fiber placement machine and/or a tool in such a manner as to lay a tow, or band of tows, at a desired location on the tool;
    the MCS also being configured for providing synchronization commands to the CCD, so that both the MCS and the CCD can be calibrated to the same position along each course;
    the CCD being configured for capturing a visual image of the actual lay-up surface of the tows, as they are laid down by the placement head, and for comparing the actual ply profile as captured in the visual image to the theoretical ply profile.

2. The apparatus of claim 1, wherein, the CCD is further configured for producing a transferable file record of results of the CCD comparison of the visual image to the theoretical ply profile.

3. The apparatus of claim 2, wherein, the CCD is further configured for detecting and recording any discrepancies and/or anomalies between the actual and theoretical ply profiles.

4. The apparatus of claim 3, wherein, the MCS is further configured for receiving the results of the CCD comparison, and providing an output for guiding an operator of the fiber placement machine to each discrepancy and/or anomaly location, to thereby facilitate evaluation, repair, or any other action that may be deemed appropriate.

5. The apparatus of claim 4, further including, a pointing device, producing an output in the form of a visible light beam directed by the MCS for indicating the location of one or more discrepancy and/or anomaly in the composite structure.

6. The apparatus of claim 5, wherein, the visible light beam is a laser beam.

* * * * *